United States Patent [19]

Wangemann et al.

[11] Patent Number: 5,304,669
[45] Date of Patent: Apr. 19, 1994

[54] PROCESS FOR THE PRODUCTION OF ALKYL SULFATE PASTES HAVING IMPROVED FLOW PROPERTIES

[75] Inventors: Frank Wangemann, Mettmann; Rainer Hofmann, Duesseldorf; Bernd Fabry, Korschenbroich; Fritz Lange, Essen, all of Fed. Rep. of Germany

[73] Assignee: Henkel Kommanditgesellschaft auf Aktien, Duesseldorf, Fed. Rep. of Germany

[21] Appl. No.: 39,367

[22] PCT Filed: Oct. 8, 1991

[86] PCT No.: PCT/EP91/01913
§ 371 Date: Apr. 16, 1993
§ 102(e) Date: Apr. 16, 1993

[87] PCT Pub. No.: WO92/06952
PCT Pub. Date: Apr. 30, 1992

[30] Foreign Application Priority Data

Oct. 17, 1990 [DE] Fed. Rep. of Germany ....... 4032909

[51] Int. Cl.$^5$ .................. C07C 303/42; C07C 303/28
[52] U.S. Cl. ........................ 558/41; 558/21; 558/34; 554/90
[58] Field of Search ................ 558/41, 21, 34; 554/90

[56] References Cited

U.S. PATENT DOCUMENTS

| 4,384,978 | 5/1983 | Ploog et al. | 252/353 |
| 4,476,037 | 10/1984 | Ploog et al. | 252/354 |
| 4,675,128 | 6/1987 | Linde et al. | 252/549 |
| 4,741,738 | 5/1988 | Friese et al. | 8/94.19 |

FOREIGN PATENT DOCUMENTS

| 0008060 | 7/1979 | European Pat. Off. . |
| 0024711 | 3/1981 | European Pat. Off. . |
| 0130753 | 1/1985 | European Pat. Off. . |
| 0178557 | 4/1986 | European Pat. Off. . |
| 1617160 | 6/1967 | Fed. Rep. of Germany . |
| 2251405 | 10/1972 | Fed. Rep. of Germany . |
| 2305554 | 2/1973 | Fed. Rep. of Germany . |
| 3447859 | 12/1984 | Fed. Rep. of Germany . |
| 0240025 | 8/1985 | Fed. Rep. of Germany . |
| 3718896 | 5/1987 | Fed. Rep. of Germany . |
| 9106532 | 5/1991 | PCT Int'l Appl. . |
| 9109009 | 6/1991 | PCT Int'l Appl. . |
| 0793427 | 4/1958 | United Kingdom . |

OTHER PUBLICATIONS

J. Falbe (ed.), "Surfactants in Consumer Products", Springer Verlag, Berlin-Heidelberg, 1987, pp. 61 to 63.

*Primary Examiner*—Marianne M. Cintins
*Assistant Examiner*—Margaret J. Page
*Attorney, Agent, or Firm*—Ernest G. Szoke; Wayne C. Jaeschke; John E. Drach

[57] ABSTRACT

The alkylsulphate pastes disclosed can be prepared by sulphonating mixtures containing a) 50-90% by weight of at least one aliphatic primary alcohol with 6-22 carbon atoms and b) 1-50% by weight of at least one unsaturated fatty acid glyceride ester derived from fatty acids having 16-22 carbon atoms and having one, two or three double bonds, with gaseous sulphur trioxide and subsequently neutralizing and hydrolysing the reaction products with aqueous bases in such a way that pastes with solids contents of 30-80% by weight are obtained.

8 Claims, No Drawings

PROCESS FOR THE PRODUCTION OF ALKYL SULFATE PASTES HAVING IMPROVED FLOW PROPERTIES

BACKGROUND OF THE INVENTION

1. Field of the Invention

This invention relates to a process for the production of alkyl sulfate pastes having improved flow properties by co-sulfonation of aliphatic alcohols and unsaturated fatty acid glyceride esters and subsequent neutralization and hydrolysis of the reaction products formed.

2. Statement of Related Art

Anionic surfactants of the alkyl sulfate type, particularly those containing $C_{16-18}$ alkyl radicals, show excellent detergent properties and are used in particular in powder-form detergents.

Powder detergents of the type in question are produced from water-containing alkyl sulfate pastes. In order to avoid unnecessary mass transport during spray drying, the water-containing surfactant pastes advantageously have a high solids content. However, alkyl sulfate pastes can only be concentrated to a certain solids content. Beyond this limit, their viscosity generally reaches such high values that the surfactant solutions can no longer be pumped, even at elevated temperatures.

There has been no shortage of attempts in the past to solve the problem posed by the high viscosity of anionic surfactant pastes. For example, the use of secondary alkane sulfonates and hydroxycarboxylic acid salts as viscosity-reducing agents for anionic surfactant concentrates is known from German patent applications DE-A-34 47 859 and DE-A-22 51 405. The viscosity of alkylbenzene sulfonate pastes can be reduced by alkoxylated alcohols [DE-A-37 18 896] or aliphatic hydrocarbons [DD-A-240 025]. Other known viscosity reducers are sulfonated aromatic compounds [DE-A-23 05 554], cumene sulfonate or acidic phosphoric acid esters [DE-B-16 17 160], polyhydric alcohols, carboxylic acids or esters thereof [EP-A-0 008 060] or mono and/or disulfates of polyalkylene glycol ethers [EP-B-0 024 711].

However, the viscosity reducers mentioned fail in cases where the viscosity of water-containing alkyl sulfate pastes has to be reduced.

Accordingly, the problem addressed by the present invention was to provide a process for the production of alkyl sulfate pastes having improved flow properties.

DESCRIPTION OF THE INVENTION

The present invention relates to a process for the production of alkyl sulfate pastes having improved flow properties, characterized in that mixtures containing a) 50 to 99% by weight of at least one aliphatic primary alcohol containing 6 to 22 carbon atoms and
b) 1 to 50% by weight of at least one unsaturated fatty acid glyceride ester derived from fatty acids containing 16 to 22 carbon atoms and 1, 2 or 3 double bonds, are sulfonated with gaseous sulfur trioxide and the reaction products are subsequently neutralized with aqueous bases and hydrolyzed so that pastes having solids concentrations of 30 to 80% by weight are obtained.

It has surprisingly been found that, after sulfonation, neutralization and hydrolysis, mixtures of components a) and b) which contain these components within the limits mentioned have a distinctly lower viscosity than sulfonation products derived from the pure starting materials. The invention includes the observation that the sulfonated mixtures produced by the process according to the invention are distinguished by improved pumpability and a lower energy demand in the spray drying process.

The aliphatic primary alcohols used as component a) in accordance with the invention are fatty alcohols such as, for example, caproic alcohol, caprylic alcohol, capric alcohol, lauryl alcohol, myristyl alcohol, cetyl alcohol, stearyl alcohol or behenyl alcohol. It is preferred to use fatty alcohols containing 12 to 18 carbon atoms and preferably 16 to 18 carbon atoms.

Other suitable alcohols are technical alcohol cuts of the type obtained, for example, in the hydrogenation of technical fatty acid methyl ester mixtures of natural origin or aldehydes from Roelen's oxo synthesis. Technical coconut oil or tallow fatty alcohol cuts are preferably used. These are primary fatty alcohols which, on average, have the following C chain distribution:

|  | Coconut oil fatty alcohol | Tallow fatty alcohol |
|---|---|---|
| $C_{10}$: | 0–3% by weight | |
| $C_{12}$: | 48–58% by weight | |
| $C_{14}$: | 19–24% by weight | 0–3% by weight |
| $C_{16}$: | 9–12% by weight | 45–55% by weight |
| $C_{18}$: | 11–14% by weight | 45–55% by weight |
| $C_{20}$: | | 0–3% by weight |

The fatty acid glyceride esters used as component b) in accordance with the invention are unsaturated mono-, di- and/or triglycerides having iodine values of 60 to 210 and preferably 100 to 130 which may be of natural or synthetic origin. The fatty acid component may contain 16 to 22 carbon atoms and 1, 2 or 3 double bonds. The glycerides of palmitoleic acid, oleic acid, elaidic acid, petroselic acid, ricinoleic acid, linoleic acid, linolenic acid or erucic acid are mentioned as examples.

As usual in oleochemistry, these glycerides may also be present in the form of technical mixtures, for example as rapeseed oil, sunflower oil, olive oil, peanut oil, coriander oil, cottonseed oil, castor oil or fish oil. In this form, the fatty acid component may also contain $C_{6-22}$ fatty acids. Rapeseed oil rich in oleic acid from new plants is preferably used.

In the process according to the invention, components a) and b) may be used in a ratio by weight of 99:1 to 50:50. Alkyl sulfate pastes having particularly advantageous performance properties are obtained when the components are used in a ratio of a to b of 95:5 to 70:30 and, more particularly, 95:5 to 90:10.

The sulfonation of the mixtures containing components a) and b) is carried out with gaseous sulfur trioxide in the same known manner as for fatty acid lower alkyl esters [J. Falbe (ed.), "Surfactants in Consumer Products", Springer Verlag, Berlin-Heidelberg, 1987, pages 61 to 63], reactors operating on the falling-film principle being preferred. The sulfur trioxide is diluted with an inert gas, preferably air or nitrogen, and used in the form of a gas mixture containing the sulfonating agent in a concentration of 1 to 8% by volume and, more particularly, 2 to 5% by volume.

The molar ratio between the mixtures containing components a) and b) and the gaseous sulfur trioxide may be from 1:0.95 to 1:1.5. To obtain a high degree of sulfonation on the one hand and to guarantee minimal discoloration of the products on the other hand, ratios of 1:1.05 to 1:1.3 have proved to be optimal. The sulfonation reaction is carried out at temperatures of 50° to 90° C. and preferably at temperatures of 40° to 80° C.

The acidic sulfonation products accumulating during the sulfonation reaction are stirred into aqueous bases, neutralized and adjusted to a pH value of 7.5 to 10.5. Suitable neutralization bases are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_2$-4-alkanolamines, for example mono-, di- and triethanolamine and primary, secondary or tertiary $C_{1-4}$ alkyl amines. The neutralization bases are preferably used in the form of 5 to 55% by weight aqueous solutions, 5 to 25% by weight aqueous sodium hydroxide solutions being preferred.

In the co-sulfonation of the aliphatic alcohols and the fatty acid glyceride esters, the corresponding alkyl sulfates are formed. The unsaturated glycerides may react off with the sulfur trioxide in various ways. For example, addition products of the SO3 with the olefinic double bond and various glyceride sulfates are formed. Finally, soaps and sulfonated soaps are also present. To avoid afteracidification, the products have to be subjected to an aftertreatment in which the neutralized products are hydrolyzed for 30 to 240 mins. at temperatures of 50° to 90° C. and at pH values of 7.5 to 8.5.

After neutralization and hydrolysis, the sulfonation products may be bleached in known manner by addition of hydrogen peroxide or sodium hypochlorite solution. 0.2 to 2% by weight hydrogen peroxide, expressed as 100% substance, or corresponding quantities of sodium hypochlorite, based on the solids content of the solution of sulfonation products, are used for this purpose. The pH value of the solutions may be kept constant using suitable buffers, for example sodium phosphate or citric acid. In addition, it is advisable to add preservatives, for example formaldehyde solution, p-hydroxybenzoate, sorbic acid or other known preservatives, for stabilization against bacterial contamination.

The following Examples are intended to illustrate the invention without limiting it in any way.

EXAMPLES

Examples 1 to 4

General Procedure for the Preparation of Tallow Alkyl Sulfate/Sulfotriglyceride Mixtures 600 g of a mixture of 70 to 95 parts by weight $C_{16/18}$ tallow alcohol (Hydrenol ® DD, hydroxyl value 215, a product of Henkel KGaA) and 5 to 30 parts by weight rapeseed oil rich in oleic acid (oleic acid content > 80% by weight) were introduced into a 1 liter sulfonation reactor equipped with jacket cooling and a gas inlet pipe and reacted at T = 80° C. with sulfur trioxide in a molar ratio of mixture to $SO_3$ of 1:1.05. The sulfur trioxide was driven out by heating from a corresponding quantity of 65% by weight oleum, diluted with nitrogen to a concentration of 5% by volume and introduced into the starting product over a period of 50 minutes. The crude sulfonation product was then neutralized with aqueous 25% by weight sodium hydroxide and hydrolyzed over a period of t=2 h at a temperature T of 80° C. and at a pH value of 8. The resulting approx. 25% by weight paste was bleached with 2% by weight, based on the solids content of the paste, of a 35% by weight hydrogen peroxide solution. The product was then adjusted to pH 7.5 with hydrochloric acid and buffered with 1% by weight, based on the solids content, of citric acid. Particulars of the reaction mixtures and the characteristic data of the products are set out in Tables 1 and 2.

The anionic surfactant content (WAS) and the unsulfonated components (US) were determined by the DGF-Einheitsmethoden, Stuttgart, 1950-1984, H-III-10 and G-II-6b. The sulfate content was calculated as sodium sulfate and the water content was determined by the Fischer method.

TABLE 1

| | Sulfonation of tallow alcohol/triglyceride mixtures | | | | | | |
|---|---|---|---|---|---|---|---|
| | a:b | a | | b | | $SO_3$ | |
| Ex. | Pts. by wt. | g | = mol | g | = mol | g | = mol |
| 1 | 95:5 | 570 | 2.22 | 30 | 0.03 | 187 | 2.34 |
| 2 | 90:10 | 540 | 2.10 | 60 | 0.06 | 182 | 2.27 |
| 3 | 80:20 | 480 | 1.87 | 120 | 0.12 | 168 | 2.10 |
| 4 | 70:30 | 420 | 1.63 | 180 | 0.18 | 152 | 1.90 | a = $C_{16/18}$ tallow alcohol
b = Rapeseed oil rich in oleic acid
Legend: Pts. by wt. = parts by weight

TABLE 2

| | Characteristic data of the products | | | |
|---|---|---|---|---|
| | WAS | US | $SO_4^{2-}$ | $H_2O$ |
| Ex. | % | % | % | % |
| 1 | 18.8 | 3.6 | 0.6 | 77.0 |
| 2 | 21.0 | 1.0 | 0.0 | 77.0 |
| 3 | 20.7 | 1.7 | 0.5 | 77.0 |
| 4 | 20.5 | 2.1 | 0.4 | 77.0 |

II. VISCOSITY OF TALLOW ALKYL SULFATE/SULFOTRIGLYCERIDE MIXTURES

Examples 5 to 8

The viscosity of the sulfonated mixtures according to Examples 1 to 4 was determined with a Brookfield viscosimeter at a temperature of 80° C. The results of the viscosity measurements are shown in Table 3.

TABLE 3

| | Viscosity measurements | |
|---|---|---|
| | Mixture of | Viscosity |
| Ex. | Example | mPas |
| 5 | 1 | 1925 |
| 6 | 2 | 635 |
| 7 | 3 | 3500 |
| 8 | 4 | 9500 |

What is claimed is:

1. A process for the production of alkyl sulfate pastes having improved flow properties comprising the steps of: (1) contacting a mixture comprising: (a) from about 50% to about 99% by weight of at least one aliphatic primary alcohol containing 6 to 22 carbon atoms and, (b) from about 1% to 50% by weight of at least one unsaturated fatty acid glyceride ester derived from fatty acids containing 16 to 22 carbon atoms and 1, 2 or 3 double bonds with gaseous sulfur trioxide to produce a sulfonated product; (2) neutralizing and hydrolyzing said sulfonated product to form a paste having a solids concentration of from about 30% to about 80% by weight.

2. The process of claim 1 wherein said aliphatic primary alcohol is a hydrogenated tallow alcohol containing 16 to 18 carbon atoms.

3. The process of claim 1 wherein said unsaturated fatty acid glyceride ester is a triglyceride having an iodine value of 60 to 210.

4. The process of claim 1 wherein the weight ratio of (a)/(b) is from about 95:5 to about 70:30.

5. The process of claim 1 wherein step (1) is carried out at a temperature of from about 30° C. to 90° C.

6. The process of claim 1 wherein the molar ratio of (a)+(b)/sulfur trioxide is from about 1:0.95 to about 1:1.5.

7. The process of claim 1 wherein neutralization is carried out with from about 5% to about 55% by weight of an aqueous base selected from the group consisting of an alkali metal hydroxide, alkaline earth metal oxide and hydroxide, ammonia, a mono-, di- and tri-$C_{2-4}$-alkanolamine and a primary, secondary and tertiary $C_{1-4}$ alkyl amine.

8. The process of claim 1 wherein the hydrolysis is carried out at pH of from about 7.5 to about 8.5 and at a temperature of from about 50° C. to about 90° C. and for a period of time from about 30 minutes to about 240 minutes.

* * * * *